United States Patent [19]

Crenshaw et al.

[11] Patent Number: 5,618,816
[45] Date of Patent: Apr. 8, 1997

[54] ANTIMIGRAINE 1,2,5-THIADIAZOLE DERIVATIVES OF INDOLYLALKYL-PYRIDNYL AND PYRIMIDINYLPIPERAZINES

[75] Inventors: Ronnie R. Crenshaw, Dewitt, N.Y.;
Edward H. Ruediger, Quebec, Canada;
David W. Smith, Madison, Conn.;
Carola Solomon, Quebec, Canada;
Joseph P. Yevich, Southington, Conn.

[73] Assignee: Bristol-Myers Squibb Company, New York, N.Y.

[21] Appl. No.: 396,825

[22] Filed: Mar. 2, 1995

[51] Int. Cl.$^6$ ............. C07D 417/14; C07D 403/14; A61K 31/495; A61K 31/505
[52] U.S. Cl. ............. 514/253; 514/254; 544/295; 544/364; 544/367
[58] Field of Search ............. 544/367, 295, 544/364; 514/253, 254

[56] References Cited

U.S. PATENT DOCUMENTS

| | | | |
|---|---|---|---|
| 4,374,248 | 2/1983 | Crenshaw et al. | 548/135 |
| 4,440,933 | 4/1984 | Montzka et al. | 546/193 |
| 4,600,779 | 7/1986 | Crenshaw et al. | 548/135 |
| 4,954,502 | 9/1990 | Smith et al. | 514/253 |
| 5,077,293 | 12/1991 | Smith et al. | 514/253 |
| 5,300,506 | 4/1994 | Smith et al. | 514/253 |
| 5,382,586 | 1/1995 | Merce-Vidal et al. | 514/254 |
| 5,434,154 | 7/1995 | Smith et al. | 514/249 |

FOREIGN PATENT DOCUMENTS

| | | |
|---|---|---|
| 354094 | 2/1990 | European Pat. Off. . |
| 2124210 | 2/1984 | United Kingdom . |
| 2162522 | 2/1986 | United Kingdom . |

OTHER PUBLICATIONS

"Drugs Used to Treat Migraine and Other Headaches," *Drug Evaluations*, 6th edition, 1986, pp. 239–253.

*Primary Examiner*—Matthew V. Grumbling
*Attorney, Agent, or Firm*—Richard P. Ryan

[57] ABSTRACT

A series of novel 5-(3,4-diamino-1,2,5-thiadiazole and S-oxide) derivatives of indolylalkylpiperazinyl pyridines and pyrimidines of Formula I are intended for use in the alleviation of vascular headaches.

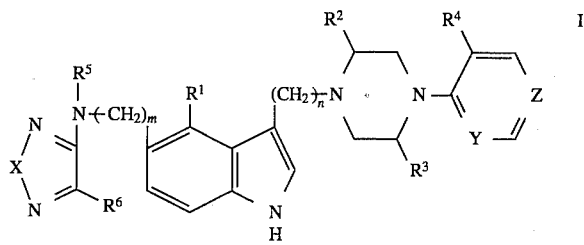

In Formula I, X is selected from S, SO and $SO_2$.

14 Claims, No Drawings

ANTIMIGRAINE 1,2,5-THIADIAZOLE DERIVATIVES OF INDOLYLALKYL-PYRIDNYL AND PYRIMIDINYLPIPERAZINES

BACKGROUND OF THE INVENTION

This invention generally pertains to heterocyclic carbon compounds having drug and bio-affecting properties and to their preparation and use. In particular, the invention is concerned with 1,4-disubstituted piperazine derivatives wherein one substituent moiety is a 1,2,5-thiadiazole; 1,2,5-thiadiazole-1-oxide, or 1,2,5-thiadiazole-1,1-dioxide-substituted indol-3-yl-alkyl group and the other moiety is a pyridinyl or pyrimidinyl ring. These compounds possess a unique serotonergic profile as well as metabolic stability that renders them useful in treatment of vascular headache, such as migraine or cluster type.

Dowie, et al. disclosed a series of 3-alkylamino-indole derivatives as being potentially useful for the treatment of migraine in a published patent application, GB 2,124,210. One member of this series of compounds was specifically claimed in a later patent application of Oxford, GB 2,162,522, published Feb. 5, 1986. This particular compound is known in the literature as sumatriptan (i).

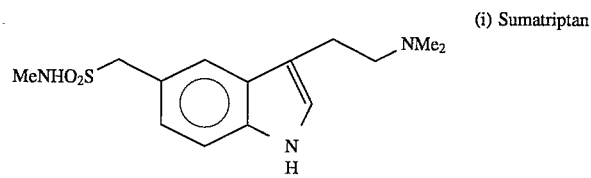

(i) Sumatriptan

A series of novel indoline derivatives was disclosed by Manoury, et al., in European patent application EPA 354,094. These compounds are described as being useful for treatment of various CNS disorders including depression, anxiety and migraine. Included among these art compounds are those of formula (ii)

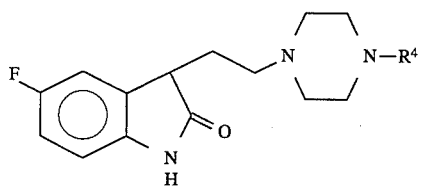

(ii)

wherein $R^4$ is aryl, pyridine or quinoline moieties.

Smith, et al., in U.S. Pat. No. 4,954,502 have disclosed a series of 1,4-disubstituted piperazine derivatives of formula (iii) which are useful as antidepressant agents.

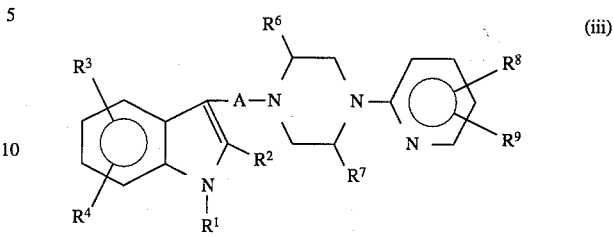

The indolyl substituents $R^3$ and $R^4$ were hydrogen, alkyl, alkoxy, alkylthio, halogen, carboxamide, and trifluoromethyl.

Another series of antidepressant 1,4-disubstituted piperazines where pyrimidine moieties were used instead of pyridine was set forth by Smith, et al., in U.S. Pat. No. 5,077,293.

More relevant background is U.S. Pat. No. 5,300,506, an earlier disclosure of antimigraine alkoxypyrimidine derivatives of formula (iv)

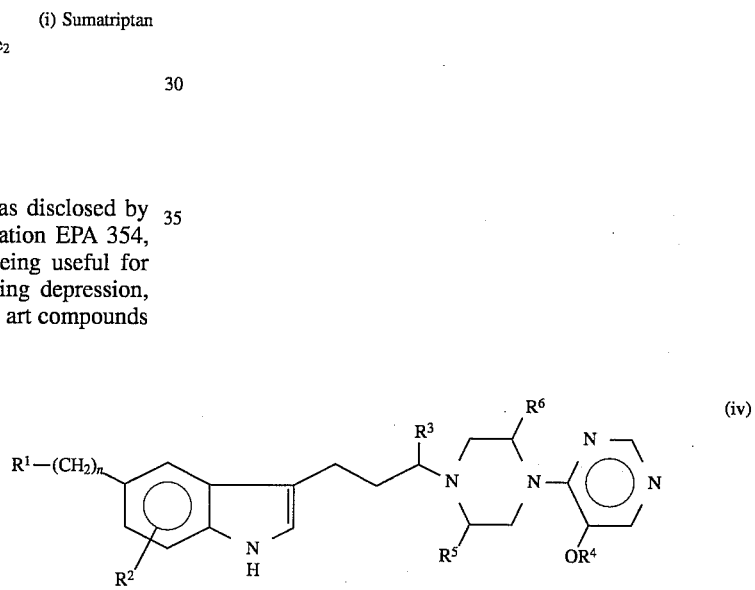

wherein the 5-indole substituents ($R^1$) included inter alia amino, alkoxy, amido, alkylsulfonylamino, and

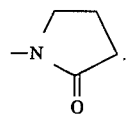

Most relevant is believed to be our earlier patent application, U.S. Ser. No. 08/122,266, that disclosed antimigraine compounds of formula (v):

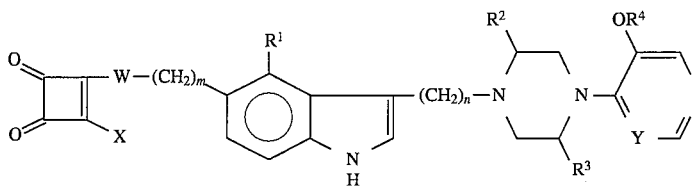

None of these art compounds suggest the instant novel 5-thiadiazole (and its oxides)-substituted-indol-3-ylalkyl derivatives of pyridinyl or pyrimidinylpiperazines for the treatment of migraine and cluster-type headaches.

Migraine is a member of a broader class of headache that also comprises cluster headaches and other headaches believed to have a vascular implication in their etiology. These headaches are often classified as vascular headaches. For a current summary of headache and its treatment see: Chapter 13: "Drugs Used to Treat Migraine and Other Headaches" in *Drug Evaluation, 6th Edn.*, 1986, pages 239–253, American Medical Association. W. B. Saunders Co., Philadelphia, Pa.

Frequent irregularly-occurring episodes of headache afflict a large number of people but are usually acute in nature and of short duration. Relief of this type of headache is typically provided by mild analgesics such as aspirin or acetaminophen. Such headaches are quite common and, while painful and perhaps annoying, are seldom incapacitating and debilitating. Chronic recurrent headaches of the vascular category, however, usually lead to patient consultation with a physician due to pain severity which is often incapacitating.

Although there is no universally accepted classification system for headache, vascular headache, for the purposes of the present invention, refers mainly to migraine and cluster headaches. Migraine includes the common or classical type as well as migraine variants which would be familiar to one skilled in the art. Other subtypes such as toxic vascular and hypertensive headaches, chronic paroxysmal hemicrania, as well as some muscle-contraction and combined or mixed vascular-muscle headaches may also fall into a vascular-related headache category and be treatable by the present invention. It is appreciated by one skilled in the art that no single therapy is effective in all patients diagnosed with the same subtype of headache, thereby raising further uncertainties about headache classification.

Drugs that have historically been most commonly used in treatment of headache fall into the following group:

Ergot Alkaloids,
Beta-blocking Agents,
Calcium Channel Blocking Agents,
Antidepressants, and
Mixtures of these.

Management of recurring vascular headache is complicated by the lack of a single therapy which is effective in all patients with the same headache type. A more recently available antimigraine agent, Sumatriptan, has met with some success in treating migraine in patients but still possesses shortcomings. Further complication involves the antimigraine use of drugs that can cause dependence with extended use, such as ergotamine. Another important consideration for the present invention is that the more potent antimigraine agents in current use, e.g. the ergots and methysergide, produce severe use-limiting side-effects with long-term usage.

Thus, there is a need for a safe and effective drug for the treatment of migraine and related disorders which can be used either to abort a threatened headache or to alleviate an established headache.

The objectives of the present invention relate to the use of novel 5-(3,4-diamino-1,2,5-thiadiazole-1-oxide)-substituted indol-3-ylalkyl derivatives of pyridinyl- and pyrimidinylpiperazines to provide treatment of vascular headaches, particularly migraine and cluster-types; to processes for their preparation; and to their pharmaceutical compositions and medical usage.

SUMMARY AND DETAILED DESCRIPTION OF THE INVENTION

The method of the present invention is intended for the alleviation of vascular or vascular-related headache of which migraine and cluster are the best known specific examples. The method essentially involves administration of a 5-thiadiazole (or an S-oxide)-substituted indol-3-ylalkyl derivative of a pyridinyl or pyrimidinylpiperazine, or a pharmaceutically acceptable salt and/or solvate thereof, to a human in need of such treatment. For use in the instant method, oral and transnasal administration of pharmaceutical compositions containing the subject antimigraine agents are preferred.

In a broad aspect, the present invention is concerned with indol-3-ylalkyl derivatives of pyridinyl or pyrimidinylpiperazines having useful antimigraine serotonergic properties and characterized by Formula I.

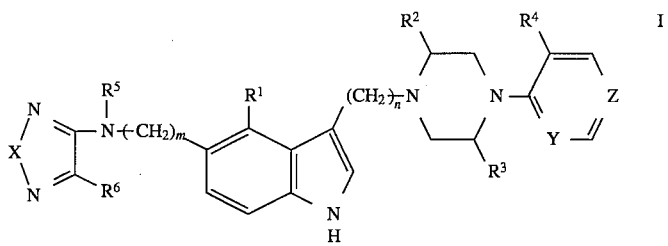

In Formula I, $R^1$ is a substituent selected from hydrogen, halogen, lower alkyl and lower alkoxy.

$R^2$, $R^3$ and $R^5$ are independently selected from hydrogen and lower alkyl. In preferred compounds, $R^2$ and $R^3$ are not lower alkyl at the same time.

$R^4$ is lower alkoxy.

$R^6$ is selected from amino, lower alkylamino, di-lower alkylamino and lower alkoxy.

The integers 1 to 3 or zero can be selected for m, while n can be the integers 1 to 5. In preferred compounds, m is zero and n is 3.

X is selected from S, SO and $SO_2$. Preferred compounds are those wherein X is SO.

Y and Z are independently selected from N and CH with the proviso that both Y and Z cannot be CH simultaneously.

Additionally, compounds of Formula I also encompass all pharmaceutically acceptable acid addition salts and/or solvates thereof. The present invention is also considered to include stereoisomers as well as optical isomers, e.g. mixtures of enantiomers as well as individual enantiomers and diasteromers, which arise as a consequence of structural asymmetry in certain compounds of the instant series. Separation of the individual isomers is accomplished by application of various methods which are well known to practitioners in the art.

The term "lower alkyl" refers to both straight and branched chain carbon radicals of from 1 to 4 carbon atoms inclusive. Illustrative of these radicals are carbon chains which can be methyl, ethyl, propyl, isopropyl, 1-butyl, 1-methylpropyl, 2-methylpropyl.

Lower alkoxy refers to $C_{1-4}$ alkyl groups connected to an oxygen atom. The thiadiazolyl moiety encompasses the sulfoxide (SO) and sulfone ($SO_2$) derivatives also.

By appropriate selection of Y and Z either a pyridine or a pyrimidine ring is designated.

The pharmaceutically acceptable acid addition salts of the invention are those in which the counter-ion does not contribute significantly to the toxicity or pharmacological activity of the salt and, as such, they are the pharmacological equivalents of the bases of Formula I. They are generally preferred for medical usage. In some instances, they have physical properties which makes them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of a Formula I base with the selected acid preferably by contact in solution employing an excess of commonly used inert solvents such as water, ether, benzene, methanol, ethanol, ethyl acetate and acetonitrile. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include sulfuric, phosphoric, hydrochloric, hydrobromic, hydroiodic, citric, acetic, benzoic, cinnamic, fumaric, mandelic, phosphoric, nitric, mucic, maleic, isethionic, palmitic, heptanoic, and others.

The compounds of Formula I can be prepared by adaptation of the synthetic processes and compounds shown in Schemes A and B.

Certain compounds and their syntheses will also be set forth in more detail in the Specific Embodiments section, infra.

In the synthetic schemes, $R^1$ through $R^6$, X, Y, Z, m and n are as defined supra. The symbol Q represents a synthetic organic leaving group moiety such as tosyl, mesyl, halide, sulfate, phosphate, and so forth.

Scheme A sets out the processes for synthesizing compounds of Formula I wherein X is SO or $SO_2$. Scheme B illustrates compounds wherein X is S. The processes proceed via the 5-amino-substituted intermediates of formula (6) wherein the heterocyclic-substituted-piperazine moiety is already incorporated into the molecular structure. Modification of the synthetic path can be made to determine not only the desired $R^6$-substituent on the thiadiazole moiety (e.g. $R^4$ or $NR^2R^3$ as shown) but also the desired identity of the $R^5$ substituent, either H or alkyl, as well. To synthesize product wherein $R^5$ is alkyl, intermediate (6) is mono-N-alkylated prior to further reaction in Schemes A and B.

The synthetic processes illustrated in Scheme A essentially involve the buildup of the indolylalkylpiperazinylheterocyclic moiety with a terminal amino group attached to the 5-position of the indole ring, e.g. compound (6). This intermediate is reacted with either the 1-oxide or 1,1-dioxide form of a 3,4-dialkoxythiadiazole (3) to yield a formula I product wherein $R^6$ is alkoxy ($R^4$). This product will provide, upon displacement of the thiodiazole's alkoxy moiety with an amine; a formula I product wherein $R^6$ is an amino group, e.g. compound (I-2). As stated above, intermediate compound (6) can be N-alkylated at the 5-indolyl-amino terminus to provide intermediates and products wherein $R^5$ is an alkyl group.

The Scheme B processes involve synthesis of products bearing the thiadiazole ring (X is only S). This process, previously disclosed in U.S. Pat. Nos. 4,440,933 and 4,600,779 for a series of histamine $H_2$-receptor antagonists; is applicable here. These U.S. patents are hereby incorporated by reference. Essentially, Scheme B illustrates reaction of a compound (6) intermediate with a 1,2-dialkoxy substituted ethanediimide to provide an intermediate compound of formula (7). Reaction of compound (7) with N,N'-thiobisphthalimide results in the thiadiazole analog product (I-3). As in Scheme A, the thiadiazolyl alkoxy substituent ($R^6=R^4$) of compound (I-3) can be displaced by an amine to yield product of formula (I-4) wherein $R^6$ is an amino function.

Scheme C deals with synthetic pathways for intermediate compounds for use in Schemes A and B; setting forth, by way of example, some typical syntheses which provide starting intermediates for these schemes.

The reactions employed in Schemes A, B and C and their application are familiar to the practitioner skilled in organic synthesis and modifications of conditions and reagents would be readily understood. The skilled synthetic chemist would know how to adapt these processes for preparation of specific Formula I compounds including other compounds embraced by this invention but not specifically disclosed. Variations of the methods to produce the same compounds in somewhat different fashion will also be evident to one skilled in the art. To provide greater detail in description, representative synthetic examples are provided infra in the Specific Embodiments section.

Serotonin has been linked to the pathophysiology of migraine by accumulating evidence, including increased excretion of serotonin metabolites following a migraine attack and a reduction in the serotonin content of blood platelets during the migraine headache. This latter effect appears to be specific for migraine and not a result of pain or stress. (Anthony, et al., "Plasma serotonin in migraine and stress," *Arch. Neurol.* 1967, 16:544–552). More importantly, intramuscular injection of reserpine lowers plasma serotonin and induces a typical migraine-type headache in migraine sufferers. This induced headache can be alleviated by slow I.V. injection of serotonin creatinine sulfate. (Kimball, et al., "Effect of serotonin in migraine patients," *Neurology N.Y.,* 1960, 10:107–111).

Although serotonin has been shown to be effective in treating migraine attacks, its use in migraine is precluded by its side-effects such as restlessness, nausea, faintness, hyperpnea, facial flushing and parasthesias. (Lance, et al., "The control of cranial arteries by humoral mechanisms and its relation to the migraine syndrome," *Headache,* 1967, 7:93–102). For this reason, more specific serotonin agents, which would treat the migraine without all of the other actions, are potentially useful antimigraine medicaments. Accumulating findings have led to the perception that compounds with selectivity for the 5-$HT_{1D}$ sub-type of serotonin receptors would be clinically efficacious in the treatment of migraine. In this regard, the compounds of the instant invention demonstrate potent affinity at the 5-$HT_{1D}$ site. Formula I compounds of interest have potencies wherein $IC_{50}$ values of these compounds are less than 100 nmolar. Preferred compounds have $IC_{50}$ values below 10 nmolar.

Determination of 5-$HT_{1D}$ binding properties was accomplished employing methodology such as that described by Heuring and Peroutka, *J. Neurosci.,* 7(3), 1987, 894–903; with only minor modifications. In vitro $IC_{50}$ (nM) test values were determined for the compounds of this invention employing tritiated serotonin.

In addition to the 5-$HT_{1D}$ binding test data, ability of the compounds of this invention to elicit contraction in a canine saphenous vein model further indicates usefulness in treatment of vascular headaches. Preferred compounds demonstrate potency equal to or in excess of serotonin itself. In addition, the instant compounds showed significantly greater in vitro stability on incubation in rat liver homogenate than the earlier series of indolyl-squarate compounds disclosed in U.S. Ser. No. 08/122,266. All these foregoing pharmacologic tests indicate useful antimigraine action for the compounds of this invention.

Another aspect then of the instant invention provides a method for treating a migraine sufferer which comprises systemic administration to the sufferer of a therapeutically effective amount of a compound of Formula I or a pharmaceutically acceptable salt thereof. It is expected that the Formula I compounds may be administered to abort a migraine attack in its early stages as well as being administered to treat an established vascular headache.

The administration and dosage regimen of compounds of Formula I can be considered to be done in much the same manner as for the reference compound sumatriptan, cf: Oxford, GB 2,162,522A. Although the instant compounds may be administered intra-nasally and orally, the dosage and dosage regimen must in each case be carefully adjusted, utilizing sound professional judgment and considering the age, weight and condition of the recipient, the route of administration and the nature and gravity of the illness. Generally the daily dose will be from about 0.05 to about 10 mg/kg, preferably 0.1 to 2 mg/kg, when administered parenterally and from about 1 to about 50 mg/kg, preferably about 5 to 20 mg/kg, when administered orally. In some instances, a sufficient therapeutic effect can be obtained at lower doses while in others, larger doses will be required. Systemic administration refers to oral, intra-nasal, rectal and parenteral routes (i.e. intramuscular, intravenous and subcutaneous). Generally, it will be found that when a compound of the present invention is administered orally, a larger quantity of the active agent is required to produce the same effect as a smaller quantity given intra-nasally or parenterally. In accordance with good clinical practice, it is preferred to administer the instant compounds at a concentration level that will produce effective antimigraine effects without causing any harmful or untoward side effects.

The compounds of the present invention may be administered for antimigraine purposes either as individual therapeutic agents or as mixtures with other therapeutic agents. Therapeutically, they are generally given as pharmaceutical compositions comprised of an antimigraine amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g. starch) and wetting agents (e.g. sodium lauryl sulfate). Solutions or suspensions of a Formula I compound with conventional pharmaceutical vehicles are employed for intra-nasal and parenteral compositions such as an aqueous solution for intravenous injection or an oily suspension for intramuscular injection.

DESCRIPTION OF SPECIFIC EMBODIMENTS

The compounds which constitute this invention, their methods of preparation and their biologic actions will appear more fully from consideration of the following examples, which are given for the purpose of illustration only and are not to be construed as limiting the invention in sphere or scope. In the following examples, used to illustrate the foregoing synthetic processes, temperatures are expressed in degrees Celsius and melting points are uncorrected. The nuclear magnetic resonance (NMR) spectral characteristics refer to chemical shifts ($\delta$) expressed as parts per million (ppm) versus tetramethylsilane (TMS) as reference standard. The relative area reported for the various shifts in the $^1$H NMR spectral data corresponds to the number of hydrogen atoms of a particular functional type in the molecule. The nature of the shifts as to multiplicity is reported as broad singlet (bs), singlet (s), multiplet (m), heptet (hept), quartet (q), triplet (t) or doublet (d). Abbreviations employed are DMSO-$d_6$ (deuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed either neat or using potassium bromide (KBr) as diluent. The elemental analyses are reported as percent by weight.

The following examples describe in detail the preparation of compounds of Formula I, as well as synthetic intermediates in each process. It will be apparent to those skilled in the art that modifications, both of materials and methods, will allow preparation of other compounds disclosed herein. From the foregoing description and the following examples it is believed that one skilled in the art is able to use the invention to the fullest extent. In addition, examples of synthesizing certain intermediates and 1,2,5-thiadiazole compounds having amine substituents at the 3- and 4-positions have been disclosed. See, e.g. Crenshaw and Algieri, U.S. Pat. Nos. 4,374,248 and 4,600,779; Montzka, U.S. Pat. No. 4,440,933. These U.S. patents are hereby incorporated by reference to provide enablement for certain of the instant intermediates and products.

A. Preparation of Intermediate Compounds

Some representative procedures for preparation of synthetic intermediate compounds contained in the processes of the schemes are given hereinbelow. Most starting materials and certain intermediates are either commercially available or procedures for their synthesis are readily available in the chemical literature allowing their full utilization by one skilled in the art of organic synthetic chemistry.

EXAMPLE 1

5-[(5-Nitro-1H-indol-3-yl)methyl]-2,2-dimethyl-1,3-dioxane-4,6-dione

An adaption of the procedure of Flaugh[1] was used. Thus, a solution of 5-nitroindole (50.0 g, 0.32 mol), Meldrum's acid (46.0 g, 0.32 mol), 37% aqueous formaldehyde (26.0 mL, 0.32 mol) and proline (1.8 g, 0.016 mol) in 200 mL of acetonitrile was stirred at room temperature for 18 h. The resulting thick yellow slurry was filtered and the filtercake was washed with acetonitrile, then acetone and finally with ether. This material was dried/in vacuo to give the title compound (80.0 g, 81%) as a bright yellow solid, mp 182° C. (dec). The mother liquor was concentrated and then diluted with $H_2O$, and the resulting solid was collected, washed and dried as before to give a second crop of the product (7.0 g) as a darker yellow solid. Total yield=87.0 g (89%): IR (KBr) 3330, 1767, 1732 cm$^{-1}$; $^1$H NMR (DMSO-d$_6$, 200 MHz) δ11.64 (s, 1H), 8.63 (d, J=2.2 Hz, 1H), 7.96 (dd, J=9.0, 2.2 Hz, 1H), 7.49 (d, J=9.0 Hz, 1H), 7.33 (d, J=2.2 Hz, 1H), 4.84 (t, J=4.6 Hz, 1H), 3.45 (d, J=4.5 Hz, 2H), 1.78 (s, 3H), 1.55 (s, 3H). Anal. Calcd for $C_{15}H_{14}N_2O_6$: C, 56.60; H, 4.43; N, 8.80. Found: C, 56.62; H, 4.41; N, 8.91.

[1]D. S. Farlow, M. E. Flaugh, S. D. Horvath, E. R. Lavignino, P. Pranc, *Org. Prep. Proc. Int.*, 1981, 13, 39.

EXAMPLE 2

Ethyl 5-nitro-3-(1H-indole)propionate

To a solution of [5-(5-nitroindol-3-yl)methyl]-2,2-dimethyl-1,3-dioxane-4,6-dione (10.0 g, 0.031 mol) in a mixture of pyridine (80 mL) and absolute ethanol (20 mL) was added 0.1 g of copper powder and the mixture was heated to reflux under Ar for 2 h. The cooled mixture was filtered and the filtrate was evaporated. The resulting residue was triturated with ether-dichloromethane to give the title compound (7.3 g, 89%) as a solid, mp 118°–121° C.: IR (KBr) 3330, 1730 cm$^{-1}$; $^1$H NMR (DMSO-d$_6$, 200 MHz) δ11.59 (br s, 1H), 8.53 (d, J=2.2 Hz, 1H), 7.97 (dd, J=9.0, 2.3 Hz, 1H), 7.49 (d, J=9.0 Hz, 1H), 7.40 (d, J=2.1 Hz, 1H), 4.03 (q, J=7.1 Hz, 2H), 3.02 (t, J=7.4 Hz, 2H), 2.67 (t, J=7.4 Hz, 2H), 1.13 (t, J=7.1 Hz, 3H).

EXAMPLE 3

3-(3-Hydroxypropyl)-5-nitro-1H-indole

To a suspension of 95% LiAlH$_4$ (2.20 g, 0.058 mol) in 60 mL of dry THF was added a solution of ethyl 5-nitro-3-indolepropionate (7.30 g, 0.028 mol) in 100 mL of dry THF, at 0° C. under Ar. After stirring for 20 min, the mixture was quenched by the cautious addition of 3 mL of $H_2O$. The resulting suspension was stirred for 10 min and then it was filtered and the filtercake was washed with additional THF. The filtrate was evaporated and the residue was taken up in ether, dried (Na$_2$SO$_4$) and evaporated, and the resulting solid was triturated with hexane to give the title compound (4.30 g, 70%) as a yellow solid, mp 107°–110° C.: IR (KBr) 3480, 3180, 1625 cm$^{-1}$; $^1$H NMR (CDCl$_3$, 200 MHz) δ8.60 (d, J=2.1 Hz, 1H), 8.35 (br s, 1H), 8.11 (dd, J=9.0, 2.2 Hz, 1H), 7.38 (d, J=8.9 Hz, 1H), 7.16 (m, 1H), 3.75 (t, J=6.2 Hz, 2H), 2.91 (t, J=7.2 Hz, 2H), 2.07–1.93 (m, 2H), 1.37 (br s, 1H).

EXAMPLE 4a

3-(3-Bromopropyl)-5-nitro-1H-indole

To a solution of triphenylphosphine (6.70 g, 0.025 mol) in 80 mL of acetonitrile was added a solution of 3-[3-hydroxypropyl]-5-nitro-1H-indole (Example 3) (4.30 g, 0.020 mol) in 75 mL of acetonitrile, followed by a solution of CBr$_4$ (9.00 g, 0.027 mol) in 25 mL of acetonitrile, at 0° C. under Ar. The mixture was stirred at room temperature for 3 h and then it was evaporated and the residue was chromatographed (SiO$_2$/ethyl acetate-hexane, 1:9 then 1:4) to give the title compound (4.60 g, 84%) as a solid, mp 92°–95° C.: IR (neat) 3420, 1330 cm$^{-1}$; $^1$H NMR (CDCl$_3$, 200 MHz) δ8.59 (d, J=2.1 Hz, 1H), 8.40 (br s, 1H), 8.13 (dd, J=9.0, 2.2 Hz, 1H), 7.40 (d, J=9.1 Hz, 1H), 7.21 (d, J=2.2 Hz, 1H), 3.45 (t, J=6.4 Hz, 2H), 2.99 (t, J=7.2 Hz, 2H), 2.26 (m, 2H).

EXAMPLE 4b

3-[3-Iodopropyl]-5-nitro-1H-indole

A solution of 3-[3-hydroxypropyl]-5-nitro-1H-indole (1.13 g, 5.06 mmol) in 20 mL of acetonitrile was cooled to 0° C. and treated sequentially with triethylamine (1.05 mL, 7.59 mmol) and methanesulfonyl chloride (0.43 mL, 5.6 mmoL) and the mixture stirred for 30 min. The reaction mixture was quenched with 30 mL of water and the organic material was extracted into ethyl acetate. The organic extracts were dried (MgSO$_4$) and concentrated in vacuo. The crude residue was dissolved in 20 mL of acetonitrile containing KI (1.7 g, 10.1 mmol) and heated to reflux for 3 h. The reaction mixture was cooled and the solvent removed in vacuo. The residue was dissolved in 100 mL of ethyl acetate and washed with water. The ethyl acetate layer was dried (MgSO$_4$) and concentrated and the residue was purified by flash column chromatography (20% ethyl acetate in hexanes) to give the title compound (1.37 g, 4.20 mmol, 83%) as a yellow solid: mp 95°–98° C.; $^1$H NMR (DMSO-d$_6$, 300 MHz) δ8.53 (d, J=2.3 Hz, 1H), 7.97 (dd, J=2.3, 9.0 Hz, 1H), 7.51 (d, J=9.0 Hz, 1H) 7.43 (s, 1H), 3.30 (t, J=6.7 Hz, 2H), 2.84 (t, J=7.7 Hz, 2H), 2.11 (m, 2H); IR (KBr) 1330, 1510, 810 cm$^1$; MS (m/e) 330 (M$^+$). Anal. Calcd for $C_{11}H_{11}IN_2O_2$: C, 40.02, H 3.36, N 8.48. Found: C, 40.26; H, 3.27; N, 8.51.

EXAMPLE 5a

3-[3-[4-(5-Methoxy-4-pyrimidyl)-1-piperazinyl]propyl]-5-nitro-1H-indole

A mixture of 5-nitro-3-(3-bromopropyl)indole (0.57 g, 2.0 mmol), 1-(5-methoxy-4-pyrimidyl)piperazine, (0.47 g, 2.4 mmol), KI (0.40 g, 2.4 mmol) and diisopropylethylamine (1.75 mL, 10.0 mmol) in 20 mL of acetonitrile was heated to reflux under Ar for 6 h. The cooled reaction mixture was diluted with ethyl acetate and washed (H$_2$O, brine). The aqueous phase was back-extracted with dichloromethane and the combined organic phase was washed (H$_2$O, brine), dried (Na$_2$SO$_4$) and evaporated. The resulting residue was chromatographed (SiO$_2$/CH$_2$Cl$_2$-MeOH, 95:5) to give a solid which was triturated with dichloromethane-hexane to afford the title compound (0.55 g, 70%) as a yellow solid, mp 163°–166° C.: IR (KBr) 3440, 3175, 1578, 1320 cm$^{-1}$; $^1$H NMR (CDCl$_3$, 200 MHz) δ8.60 (d, J=2.1 Hz, 1H), 8.47 (br s, 1H), 8.33(s, 1H), 8.11 (dd, J=9.0, 2.2 Hz, 1H), 7.89 (s, 1H), 7.38 (d, J=9.0 Hz, 1H), 7.18 (d, J=2.0 Hz, 1H), 3.86 (s, 3H), 3.8–3.9 (m, 4H), 2.86 (t, J=7.4 Hz, 2H), 2.59 (t, J=4.9 Hz, 4H), 2.50 (t, J=7.5 Hz, 2H), 2.05–1.90 (m, 2H). Anal. Calcd for $C_{20}H_{24}N_6O_3 \cdot H_2O \cdot 0.1 CH_2Cl_2$: C, 57.08; H, 6.24; N, 19.87. Found: C, 57.37; H, 5.85; N, 19.53.

EXAMPLE 5b

3-[3-[4-(3-Methoxy-4-pyridinyl)-1-piperazinyl]propyl]-5-nitro-1H-indole

A mixture of 3-[3-iodopropyl]-5-nitro-1H-indole (1.4 g, 4.2 mmol), 1-(3-methoxy-4-pyridinyl)-piperazine (0.98 g, 5.09 mmol) and $K_2CO_3$ (1.4 g, 10.2 mmol) in 30 mL of acetonitrile was heated to reflux for 4 h. The reaction mixture was cooled and stirred for 12 h. The solvent was removed and the residue dissolved in ethyl acetate and water. The aqueous layer was separated and extracted with ethyl acetate. The organic extracts were dried ($MgSO_4$) and concentrated, and the gummy residue was purified by flash silica gel chromatography (5% methanol in dichloromethane as eluant) to give 3-[3-[4-(3-methoxy-4-pyridinyl)-1-piperazinyl]propyl]-5-nitro-1H-indole, (0.6 g, 36%) as a yellow solid: IR (KBr) 3600, 2400, 1600, 1520, 1330, 1250, 815 cm$^{-1}$; $^1$H NMR (DMSO-d$_6$, 300 MHz) $\delta$8.52 (d, J=2.2 Hz, 1H), 8.10 (s, 1H), 8.02 (d, J=5.3 Hz, 1H), 7.96 (dd, J=2.3, 9.0 Hz, 1H), 7.48. (d, J=9.0 Hz, 1H), 7.42 (s, 1H), 6.81 (d, J=5.4 Hz, 1H), 3.84 (s, 3H), 3.21 (br s, 4H), 3.07 (dd, J=6.4, 14.7 Hz, 2H), 2.79 (t, J=14.7 Hz, 2H), 2.66 (br s, 4H), 1.97 (m, 2H); MS (m/e) 395 (M$^+$).

EXAMPLE 5c

3-[3-[4-(2-Pyridinyl)-1-piperazinyl]propyl]-5-nitro-1H-indole

A mixture of 3-[3-bromopropyl]-5-nitro-1H-indole (1.4 g, 4.2 mmol), 1-(2-pyridinyl)-piperazine, (0.98 g, 5.09 mmol) and $K_2CO_3$ (1.4 g, 10.2 mmol) in 30 mL of acetonitrile was heated to reflux for 4 h. The reaction mixture was cooled, the solvent was removed and the residue dissolved in ethyl acetate and water. The aqueous layer was separated and extracted with ethyl acetate. The organic extracts were dried ($MgSO_4$) and concentrated, and the gummy residue purified by flash silica gel chromatography (5% methanol in dichloromethane) to give 3-[3-[4-(2-pyridinyl)-1-piperazinyl]propyl]-5-nitro-1H-indole, (0.6 g, 36%) as a yellow solid: IR(KBr) 3182, 1520, 1330 cm$^{-1}$; $^1$H NMR (DMSO-d$^6$, 300 MHz) $\delta$8.52 (d, J=2.24 Hz, 1H), 8.80 (dd, J=1.8, 4.8 Hz, 1H), 7.95 (dd, J=2.25, 9.0 Hz, 1H), 7.52–7.49 (m, 2H), 7.41 (s, 1H), 6.79 (d, J=8.6 Hz, 1H), 6.60 (t, J=6.6 Hz, 1H), 3.46 (t, J=4.7 Hz, 4H), 2.78 (t, J=7.4 Hz, 2H), 2.42 (t, J=5.0 Hz, 4H), 2.34 (t, J=6.9 HZ, 4H), 1.82 (dt, J=7.4, 6.9 Hz, 2H); MS (m/e) 365 (M$^+$). Anal. Calcd for $C_{20}H_{23}N_5O_2$: C, 65.73, H, 6.34, N 19.16; found C, 65.35, H, 6.26, N, 18.87.

EXAMPLE 5d

3-[3-[(3-Methoxy-2-pyridinyl)-1-piperazinyl]propyl]-5-nitro-1-indole

A mixture of 3-(3-bromopropyl)-5-nitro-1H-indole (0.88 g, 3.11 mmol), potassium carbonate (0.43 g, 3.11 mmol), potassium iodide (0.52 g, 3.11 mmol) and 1-(3-methoxy-2-pyridinyl)piperazine (0.60 g, 3.11 mmol) in 50 mL of acetonitrile was heated to reflux for 5 h. The mixture was cooled, filtered and concentrated. The residue was purified by flash column chromatoaraphy with 5% methanol in dichloromethane as eluant to give the title compound (1.2 g, 99%) as a yellow foam; IR(KBr) 3300, 1520, 1330, 1240 cm$^{-1}$; $^1$H NMR (DMSO-d$_6$, 300 MHz) $\delta$8.54 (d, J=2.2 Hz, 1H), 7.97 (dd, J=2.2, 9.9 Hz, 1H), 7.77(m, 1H), 7.50 (d, J=9.0 Hz, 1H), 7.44 (s, 1H), 7.24 (d, J=7.75 Hz, 1H), 6.90 (m, 1H), 3.78 (s, 3H), 3.33 (br s, 2H), 2.80 (t, J=7.3 Hz, 2H), 1.93 (m, 2H); MS (m/e) 395 (M$^+$).

EXAMPLE 6

3-[3-[4-(5-Methoxy-4-pyrimidyl)-1-piperazinyl]propyl]-5-amino-1H-indole

To a solution of 3-[3-[4-(5-methoxy-4-pyrimidyl)-1-piperazinyl]propyl]-5-nitroindole (0.550 g, 1.39 mmol) in a mixture of ethanol (120 mL) and THF (40 mL) was added 10% palladium-on-charcoal (0.30 g) and the mixture was hydrogenated on a Parr shaker at 40 psi for 18 h. The mixture was then filtered through Celite and the catalyst was washed with additional ethanol-THF. Evaporation of the filtrate gave the essentially pure title compound (0.557 g, 100%) as a brown foam. A sample of this material (0.143 g) was treated with excess methanolic HCl and the resulting solution was diluted with acetone to give a precipitate. The precipitate was filtered and then crystallized from ethanol to give 0.100 g of a purplish solid, mp 192° C. (dec): IR (KBr) 3410, 3200, 1630, 1540 cm$^{-1}$; $^1$H NMR (DMSO-d$_6$, 200 MHz) $\delta$11.22(br s, 1H), 10.20 (br s, 2H), 8.60 (m, 1H), 8.20 (s, 1H), 7.55 (d, J=1.6 Hz, 1H), 7.45 (d, J=8.6 Hz, 1H), 7.35 (d, J=2.1 Hz, 1H), 7.07 (dd, J= 8.6, 1.9 Hz, 1H), 4.89–4.82 (m, 2H), 3.91 (s, 3H), 3.8–3.0 (br m, 8H), 2.76 (m, 2H). Anal Calcd. for $C_{20}H_{26}N_6O \cdot 4 HCl \cdot H_2O$: C, 45.29; H, 6.08; N, 15.85. Found: C. 45.32; H, 5.97; N, 15.59.

EXAMPLE 7

4-Methyl-5-amino-3-(3-hydroxypropyl)indole

A. 4-Methylindole

A mixture of 3-nitro-o-xylene (13.4 mL, 0.1 mol), dimethylformamide dimethyl acetal (40 mL, 0.3 mol) and pyrrolidine (10 mL, 0.12 mol) in 200 mL of dry DMF was heated at 120°–130° C. (oil-bath temperature) under Ar for 21 h. The cooled mixture was poured into cold water (400 mL) and extracted: with ether (4×200 mL). The ethereal solution was washed (H$_2$O, 4×100 mL), dried (Na$_2$SO$_4$) and evaporated to give a dark red viscous oil. This oil was taken up in 150 mL of ethyl acetate, 1.5 g of 10% paliadium-on-charcoal was added and the mixture was hydrogenated at 50 psi on a Parr shaker for 1 h. The reaction mixture was then filtered, the catalyst was washed with additional ethyl acetate and the filtrate was evaporated to give a dark purple oil. Flash cnromatoaraphy (SiO$_2$/dichloromethane-petroleum ether, 1:1) of this oil gave pure 4-methylindole (8.85 g, 68%) as a light yellow-brown oil: $^1$H NMR (DMSO-d$_6$, 200 MHz) $\delta$11.04 (br s, 1H), 7.29(t, J=2.7 Hz, 1H), 7.21 (d, J=7.7 Hz, 1H), 6.96 (t J=7.2 Hz, 1H), 6.75 (dr, J=6.9, 0.8 Hz, 1H), 6.43 (m, 1H), 2.46 (s, 3H).

B. 1-Acety-4-methylindoline

To a solution of 4-methylindole (7.433 g, 0.0567 mol) in 100 mL of glacial acetic acid was added NaCNBH$_3$ (7.25 g, 0.12 mol) portionwise over 1.5 h. The reaction mixture was then concentrated in vacuo water was added and the solution was basified with 10N NaOH. The resulting mixture was extracted with ethyl acetate (×3) and the organic extract was washed (brine), dried (Na$_2$SO$_4$) and evaporated to give an oil. Flash chromatography (SiO$_2$/ethyl acetate-hexane, 1:4) of this oil gave pure 4-methylindoline (6.962 g, 92%) as an oil: $^1$H NMR (DMSO-d$_6$, 200 MHz) δ6.78 (t, J=7.6 Hz, 1H), 6.33 (d, J=7.4 Hz, 1H), 6.30 (d, J=7.6 Hz, 1H), 5.36 (br s, 1H), 3.38 (t, J=8.5 Hz, 2H), 2.81 (t, J=8.5 Hz, 2H), 2.11 (s, 3H).

The resulting oil (6.945 g, 0.0522 mol) was taken up in 10 mL of acetic anhydride. An exothermic reaction ensued and after 15 min the mixture had solidified. The volatiles were subsequently removed in vacuo to give a solid. Trituration of this material with ether afforded 6.317 g of 1-acetyl-4-methylindoline as a white crystalline solid, mp 110°–111° C. Evaporation of the supernatant and trituration of the resulting residue with hexane gave an additional 2.191 g of the pure product. Total yield=8.508 g (93%): IR (neat) 1649 cm$^{-1}$; $^1$H NMR (DMSO-d$_6$, 200 MHz) δ7.86 (d, J=7.9 Hz, 1H), 7.03 (t, J=7.7 Hz, 1H) , 6.80 (d, J=7.5 Hz, 1H), 4.08 (t, J=8.5 Hz, 2H), 3.03 (t, J=8.5 Hz, 2H), 2.18 (s, 3H), 2.13 (s, 3H). Anal Calcd. for C$_{11}$H$_{13}$NO: C, 75.39; H, 7.48; N, 8.00. Found: C, 75.41; H, 7.53; N, 7.95.

C. 4-Methyl-5-nitroindoline

A solution of 1-acetyl-4-methylindoline (8.260 g, 0.0372 mol) in 50 mL of concentrated H$_2$SO$_4$ was cooled at 5° C. and then HNO$_3$ was added dropwise so as to maintain an internal temperature of 5°–10° C. After the addition was completed the mixture was kept at the same temperature for 15 min and then it was poured into 500 mL of crushed ice and the resulting slurry was stirred until all the ice had melted. The suspension was then filtered, the filter-cake was washed with water and the residue was taken up in dichloromethane. The organic phase was separated and the aqueous phase was re-extracted with dichloromethane (×3). The combined organic phase was dried (Na$_2$SO$_4$) and evaporated to give a dark yellow solid. Chromatography (9×10 cm SiO$_2$ pad/dichloromethane then dichloromethane-acetonitrile, 95:5) of this solid gave an inseparable mixture of 1-acetyl-4-methyl-5-nitroindoline and 1-acetyl-4-methyl-7-nitroindoline (8.090 g, 78%), in a ratio of ca. 9:1: $^1$H NMR (DMSO-d$_6$, 200 MHz) δ7.98 (d, J=8.9 Hz, 0.88H), 7.89 (d, J=8.9 Hz, 0.88H), 7.54 (d, J=8.3 Hz, 0.12H), 7.03 (d, J=8.3 Hz, 0.12H), 4.18 (t, J=8.7 Hz, 2H), 3.14 (t, J=8.7 Hz, 2H), 2.37 (s, 3H), 2.19 (s, 3H).

To a suspension of 1-acetyl-4-methyl-5(7)-nitroindoline (8.049 g, 0.0366 mol) in 75 mL of methanol was added 25 mL of Claisen's alkali (c.f. Fieser & Fieser, *Reagents for Organic Synthesis*, Vol. 1, pg. 153) and the resulting mixture was warmed on a steam bath until it became homogeneous. The cooled reaction mixture was concentrated and then it was diluted with water and the resulting suspension was filtered to give an orange-brown solid. The filtrate was extracted with dichloromethane (×3) and the organic extract was dried (Na$_2$SO$_4$) and evaporated to give a solid. The combined solids were chromatographed (SiO$_2$/ether-hexane, 1:1 then chloroform)) to give two fractions. Fraction 1 was taken up in ether and the solution was treated with decolourizing charcoal, filtered (Celite) and evaporated to give 4-methyl-7-nitroindoline (0.575 g, 9%) as a dark orange solid, mp 125°–127° C.: IR (KBr) 3395, 1623, 1596 cm$^{-1}$; $^1$H NMR (DMSO-d$_6$, 200 MHz) δ7.83 (br s, 1H), 7.55 (d, J=8.8 Hz, 1H), 6.36 (d, J=8.8 Hz, 1H), 3.75 (t, J=8.6 Hz, 1H), 2.99 (t, J=8.6 Hz, 2H), 2.15 (s, 3H). Anal Calcd. for C$_9$H$_{10}$N$_2$O$_2$: C, 60.66; H, 5.66; N, 15.72. Found: C, 60.99; H, 5.71 N, 15.48.

Fraction 2 was rechromatographed (chloroform) to give a solid which was triturated with ether to give 4-methyl-5-nitroindoline (4.813 g, 74%) as an orange crystalline solid, mp 169°–171° C.: IR (KBr) 3330, 1598 cm$^{-1}$; $^1$H NMR (DMSO-d$_6$, 200 MHz) δ7.85 (d, J=8.8 Hz, 1H), 7.04 (br s, 1H), 6.33 (d, J=8.8 Hz, 1H), 3.63 (t, J=8.8 Hz, 1H), 2.98 (t, J=8.8 Hz, 2H), 2.38 (s, 3H) Anal Calcd. for C$_9$H$_{10}$N$_2$O$_2$: C, 60.66; H, 5.66; N, 15.72. Found: C, 60.66; H, 5.47: N, 15.74.

D. 4-Methyl-5-nitroindole

To a suspension of 4-methyl-5-nitroindoline (4.767 g, 0.0268 mol) in 100 mL of methanol was added 2,3-dichloro-5,6-dicyano-1,4-benzoquinone (6.697 g, 0.0295 mol) all at once and the resulting mixture was stirred at room temperature for 1 h. The reaction mixture was then evaporated and the residue was taken up in dichloromethane. This solution was then washed with saturated aqueous NaHCO$_3$ (×4), dried (Na$_2$SO$_4$) and evaporated to give a solid. Crystallization of this material from ethyl acetate-hexane (−20° C.) afforded 4.161 g of the title compound as greenish-gold needles, mp 179°–180° C. Chromatography of the mother liquor (SiO$_2$/ethyl acetate-hexane, 1:1 ) gave an additional 0.417 g of the pure product. Total yield=4.578 g (97%): IR (KBr) 3318, 1604, 1585 cm$^{-1}$; $^1$H NMR (DMSO-d$_6$, 200 MHz) δ11.72 (br s, 1H), 7.81 (d, J=9.0 Hz, 1H), 7.56 (t, J=2.8 Hz, 1H), 7.39 (d, J=8.9 Hz, 1H), 6.79 (m, 1H), 2.75 (s, 3H). Anal. Calcd for C$_9$H$_8$N$_2$O$_2$: C, 61.35; H, 4.58; N, 15.90. Found: C, 61.32; H, 4.40; N, 15.96.

E. 5-(4-Methyl-5-nitroidol-3-ylmethyl)-2,2-dimethyl-1,3-dioxane-4,6-dione

An adaption of the procedure of Flaugh was used. Thus, a solution of 4-methyl-5-nitroindole (0.880 g, 5.00 mmol), Meldrum's acid (0.864 g, 6.00 mmol), 37% aqueous formaldehyde (0.5 mL, 6.0 mmol) and D,L-proline (0.029 g, 0.25 mmol) in 25 mL of acetonitrile was stirred at room temperature for 72 h. The resulting yellow slurry was stored at −20° C. and then the cold mixture was filtered. The filtercake was washed with cold acetonitrile and ether, and then it was dried in vacuo to give the title compound (1.055 g, 64%) as a canary-yellow solid, mp 196°–198° C. (dec): IR (KBr) 3338, 1782, 1742 cm$^{-1}$; $^1$H NMR (DMSO-d$_6$, 200 MHz) δ11.46 (br s, 1H), 7.61 (d, J=8.9 Hz, 1H), 7.32 (d, J=8.9 Hz, 1H), 7.25 (d, J=2.4 Hz, 1H), 4.74 (t, J=5.0 Hz, 1H), 3.64 (d, J=4.9 Hz, 1H), 2.80 (s, 3H), 1.84 (s, 3H), 1.69 (s, 3H). Anal. Calcd for C$_{16}$H$_{16}$N$_2$O$_6$: C, 57.83; H, 4.85; N, 8.43. Found: C, 57.42; H, 4.68; N, 8.52.

F. Ethyl 4-methyl-5-nitro-3-indolepropionate

To a solution of 5-[(4-methy-5-nitroindol-3-yl)methyl]-2,2-dimethyl-1,3-dioxane-4,6-dione (1.009 g, 3.04 mmol) in a mixture of pyridine (18 mL) and absolute ethanol (2 mL) was added 0.05 g of copper powder and the mixture was heated to reflux under Ar for 2 h. The cooled mixture was filtered and the filtrate was evaporated in vacuo to give a viscous brown oil. This material was taken up in ethyl acetate and the solution was washed (1N HCl, saturated aqueous NH$_4$Cl, brine), dried (Na$_2$SO$_4$) and evaporated to give a yellow solid. Trituration with ether gave 423 mg of the title compound as a tan solid. An additional 166 mg of the product could be recovered by evaporation of the supernatant and retrituration with ether. Total yield=671 mg (80%). An analytical sample was crystallized from ethyl acetate-hexane to give tan crystals, mp 105°–106° C.: IR (KBr) 3340, 1717, 1517, 1335 cm$^{-1}$; $^1$H NMR (DMSO-d$_6$, 200 MHz) δ11.47 (br s, 1H), 7.63 (d, J=9.0 Hz, 1H), 7.30 (d, J=8.6 Hz, 1H), 7.28 (s, 1H), 4.06 (q, J=7.1 Hz, 2H), 3.18 (t, J=7.1 Hz, 2H), 2.77 (s, 3H), 2.68 (m, 2H), 1.16 (t, J=7.1 Hz, 3H). Anal. Calcd for C$_{14}$H$_{16}$N$_2$O$_4$: C, 60.86; H, 5.84: N, 10.14. Found: C, 60.76; H, 5.74; N, 10.00.

G. 4-Methyl-5-nitro-3-(3-hydroxypropyl)indole

To a suspension of 95% LiAlH$_4$ (0.378 g, 9.44 mmol) in 10 mL of dry THF was added a solution of ethyl 4-methyl-5-nitro-3-indolepropionate (0.650 g, 2.36 mmol) in 2 mL of dry THF, at 0° C. under Ar. After 5 min the cooling bath was removed and stirring was continued at room temperature for 30 min. The reaction was then quenched by the sequential addition of 0.4 mL of water, 0.4 mL of 15% aqueous NaOH and finally 1.2 mL of water. The resulting suspension was diluted with ethyl acetate and then it was filtered and the filtercake was washed with additional ethyl acetate. The filtrate was evaporated and the residue was chromatographed (SiO$_2$/dichloromethane-ethyl acetate, 2:1) to give the title compound (0.458 g, 83%) as a solid. An analytical sample was crystallized from ethyl acetate-hexane to give yellow-orange needles, mp 129°–130° C.: IR (KBr) 3543, 3210, 1616, 1520, 1330 cm$^{-1}$; $^1$H NMR (DMSO-d$_6$, 200 MHz) δ11.43 (br s, 1H), 7.63 (d, J=8.9 Hz, 1H), 7.30 (d, J=8.7 Hz, 1H), 7.29 (s, 1H), 4.51 (t, J=5.2 Hz, 1H), 5.20 (dt, J=6.2, 5.4 Hz, 2H), 2.91 (t, J=7.7 Hz, 2H), 2.78 (s, 3H), 1.78 (m, 2H). Anal. Calcd for C$_{12}$H$_{14}$N$_2$O$_3$: C, 61.52; H, 6.02; N, 11.96. Found: C, 61.23; H, 5.85; N, 11.90.

H. 4-Methyl-5-amino-3-(3-hydroxyoropyl)indole

To a solution of 4-methyl-5-nitro-3-(3-hydroxypropyl)indole (0.365 g, 1.56 mmol) in 20 mL of absolute ethanol was added 10% palladium-on-charcoal (0.150 g) and the mixture was hydrogenated on a Parr shaker at 50 psi for 0.5 h. The mixture was then filtered through a plug of Celite, the catalyst was washed with additional ethanol and the filtrate was evaporated to give the title compound (0.280 g, 88%) as a solid. An analytical sample was crystallized from ethyl acetate to give cream-coloured needles, mp 141°–142° C.: IR (KBr) 3388, 3180, 1618 cm$^{-1}$; $^1$H NMR (DMSO-d$_6$, 200 MHz) δ10.20 (br s, 1H), 6.87 (d, J=8.8 Hz, 1H), 6.83 (s, 1H), 6.50 (d, J=8.3 Hz, 1H), 4.43 (t, J=5.2 Hz, 1H), 4.12 (s, 2H), 3.47 (dt, J=6.4, 5.3 Hz, 2H), 2.79 (t, J=7.7 Hz, 2H), 2.31 (s, 3H), 1.73 (m, 2H). Anal. Calcd for C$_{12}$H$_{16}$N$_2$O: C, 70.55; H, 7.90; N, 13.72. Found: C, 70.41; H, 7.89; N, 13.55.

EXAMPLE 8

3,4-Dimethoxy-1,2,5-thiadiazole-1,1-dioxide

A solution of 3,4-dimethoxy-1,2,5-thiadiazole (1.48 g; 10.1 mmoles) [prepared according to the procedure described in *J. Org. Chem.*, 40, 2749 (1975)] in 20 ml of chloroform was added over a period of 1 minute to a stirred solution of m-chloroperbenzoic acid (4.11 g; 20.3 mmoles; 85% assay) in 60 ml of chloroform. After stirring at ambient temperature for 1 hour, the mixture was heated to reflux temperature for 8 hours and then stirred at ambient temperature for 1 hour. The reaction mixture was extracted with aqueous sodium bicarbonate and water, and the organic phase was dried over sodium sulfate, filtered and evaporated under reduced pressure. The residue was treated with methanol and filtered to give 1.03 g of product. Recrystallization from methanol yielded the title compound, mp 200°–202°. Anal. Calcd. for C$_4$H$_6$N$_2$O$_4$S: C, 26.97; H, 3.39; N, 15.72; S, 18.00. Found: C, 26.82; H, 3.18, N, 16.09; S, 18.00.

EXAMPLE 9

3,4-Dimethoxy-1,2,5-thiadiazole-1-oxide

A solution of dimethyl oxaldiimidate (4.0 gm; 34.5 mmole) and pyridine (5.71 ml, 5.58 gm; 70.6 mmoles) in 8 ml of CH$_2$Cl$_2$ was added dropwise to a cold solution of thionyl chloride (2.61 ml, 4.25 gm; 34.7 mmole) in 18 ml of CH$_2$Cl$_2$ under a stream of nitrogen, at such a rate that the reaction temperature remained between 0° and 15°. After stirring at ambient temperature for 20 minutes, the reaction mixture was washed with two 11 ml portions of aqueous 0.055N HCl. The aqueous phase was extracted with two 20 ml portions of CH$_2$Cl$_2$ and the combined organic phase was dried and evaporated to dryness under reduced pressure. The solid residue was recrystallized from isopropyl alcohol to give 3.0 gm of the title compound, mp 137°–139°.

B. Formula I Products

1. Formula I-1 Product (X=SO, SO$_2$)

EXAMPLE 10

3-[3-[4-(5-Methoxy-4-pyrimidyl)-1-piperazinyl]propyl]-5-(1-oxo-4-methoxy-1,2,5-thiadiazol-3-yl)aminoindole

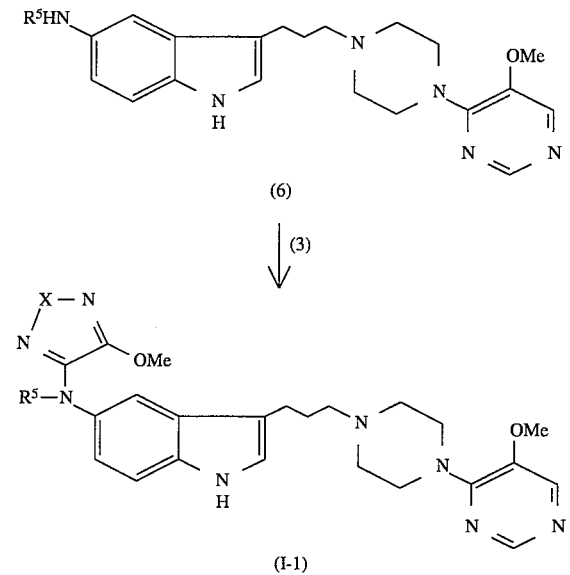

A solution of 3-[3-[4-(5-methoxy-4-pyrimidyl)-1-piperazinyl]propyl]-5-aminoindole (0.366 g, 1.0 mmol) and 3,4-dimethoxy-1,2,5-thiadiazole-1-oxide (3) (0.162 g, 1.0 mmol; see U.S. Pat. No. 4,374,248) in 20 mL of methanol was stirred at room temperature for 30 min and then it was heated to reflux for 4 h. The cooled mixture was evaporated and the residue was triturated with dichloromethane to give 0.323 g of a solid. This material was chromatographed (SiO$_2$/CH$_2$Cl$_2$-MeOH, 95:5 then CH$_2$Cl$_2$-MeOH-NH$_4$OH, 95:4.5:0.5) to give the title compound (0.150 g, 30%) as a yellow solid, mp 164° C. (dec): IR (KBr) 3330 (br), 1605, 1580, 1130 cm$^{-1}$; $^1$H NMR (DMSO-d$_6$, 400 MHz) δ10.85 (s, 1H), 10.38 (s, 1H), 8.23 (s, 1H), 8.18 (s, 1H), 8.02 (s, 1H), 7.57 (d, J=8.7 Hz, 1H), 7.34 (d, J=8.7 Hz, 1H), 7.17 (s, 1H), 4.17 (s, 3H), 3.83 (s, 3H), 3.68 (br s, 4H), 2.69 (t, J=7.4 Hz, 2H), 2.37 (t, J=7.4 Hz, 2H), 1.84 (m, 2H). Anal. Calcd for C$_{23}$H$_{28}$N$_8$O$_3$S. H$_2$O: C, 53.68; H, 5.88; N, 21.78. Found: C, 53.87; H, 5.88; N, 21.63.

2. Formula I-2 Product

EXAMPLE 11

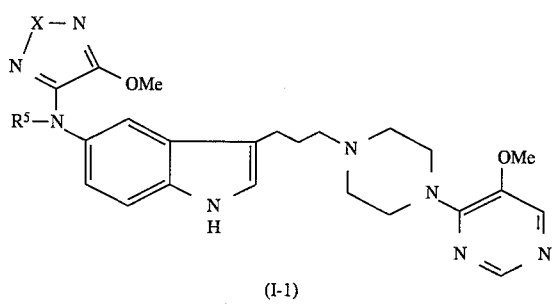

(I-1)

↓

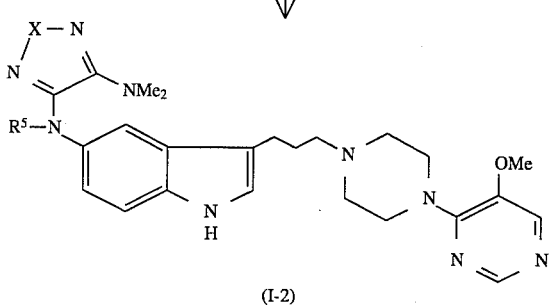

(I-2)

Anhydrous dimethylamine was bubbled into 50 mL of absolute ethanol at −10° C. for ca. 30 min. To this cold solution was added a solution of 3-[3-[4-(5-methoxy-4-pyrimidyl)-1-piperazinyl]propyl]-5-(1-oxo-4-methoxy-1,2,5-thiadiazol-3-yl)aminoindole (Example 8) (0.190 g, 0.38 mmol) and the resulting solution was stirred at room temperature for 1 h. The reaction mixture was then evaporated to give an off-white solid which was chromatographed (SiO$_2$/CH$_2$Cl$_2$-MeOH, 95:5 then CH$_2$Cl$_2$-MeOH-NH$_4$OH, 95:4.5:0.5 to 90:9:1) to give the title compound (0.130 g, 62%) as an off-white solid, mp 150° C. (dec): IR (KBr) 3310 (br), 1628, 1608, 1575 cm$^{-1}$; $^1$H NMR (DMSO-d$_6$, 200 MHz) δ10.88 (br s, 0.5H), 9.88 (br s, 0.5H), 8.51 (br s, 1H), 8.23 (s, 1H), 8.11 (s, 1H), 8.02 (s, 1H), 7.38 (s, 2H), 7.18 (s, 1H), 3.83 (s, 3H), 3.70 (br s, 4H), 3.00 (s, 3H), 2.71 (m, 2H), 2.50 (m, 9H), 1.86 (m, 2H). Anal. Calcd for C$_{24}$H$_{31}$N$_9$O$_2$S. 1.9 H$_2$O. 0.04 CH$_2$Cl$_2$: C, 52.76; H, 6.42; N, 23.04. Found: C, 52.37; H, 6.02; N, 23.50.

EXAMPLE 12

3-[3-[4-(5-Methoxy-4-pyrimidyl)-1-piperazinyl]propyl]-5-(1-oxo-4-methylamino-1,2,5-thiadiazol-3-yl)aminoindole

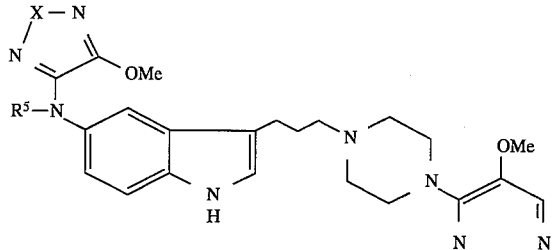

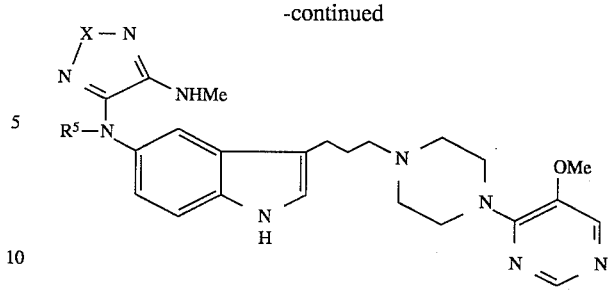

Anhydrous methylamine was bubbled into 50 mL of absolute ethanol at −10° C. for ca. 30 min. To this cold solution was added 3-[3-[4-(5-methoxy-4-pyrimidyl)-1-piperazinyl]propyl]-5-(1-oxo-4-methoxy-1,2,5-thiadiazol-3-yl)aminoindole (Example 8) (0.200 g, 0.40 mmol) and the resulting solution was stirred at room temperature for 3 h. The reaction mixture was then evaporated to give a solid which was triturated to give the essentially pure product (0.120 g, 60%) as a pale yellow solid. This material was recrystallized from aqueous DMSO to give the title compound (0.100 g, 47%) as a pale yellow solid, mp 150°–158° C.: IR (KBr) 3310 (br), 1626, 1608, 1575 cm$^{-1}$; $^1$H NMR (DMSO-d$_6$, 200 MHz) δ10.86 (br s, 1H), 9.84 (br s, 1H), 8.47 (br s, 1H), 8.22 (s, 1H), 8.09 (s, 1H), 8.01 (s, 1H), 7.37 (s, 2H), 7.17 (s, 1H), 3.82 (s, 3H), 3.67 (br s, 4H), 3.00 (br s, 3H), 2.70 (m, 2H), 2.54–2.33 (m, 6H), 1.83 (m, 2H). Anal. Calcd for C$_{23}$H$_{29}$N$_9$O$_2$S. 1.3 H$_2$O. 0.15 C$_2$H$_6$OS: C, 52.72; H, 6.17; N, 23.76. Found: C, 52.90; H, 6.21; N, 23.39.

EXAMPLE 13

3-[3-[4-(5-Methoxy-4-pyrimidyl)-1-piperazinyl]propyl]-5-(1-oxo-4-amino-1,2,5-thiadiazol-3-yl)aminoindole

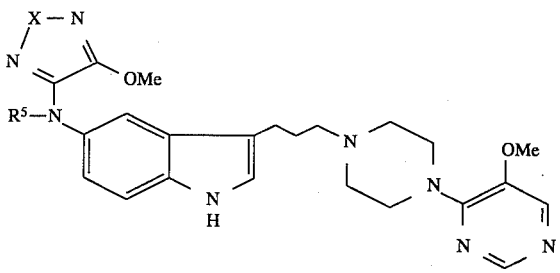

↓

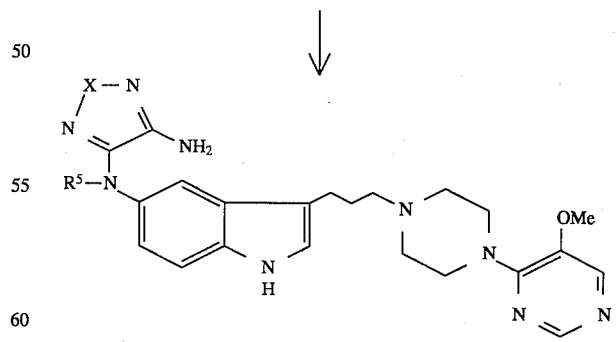

Anhydrous ammonia was bubbled into 40 mL of absolute ethanol at −10° C. for ca. 15 min. To this cold solution was added a solution of 3-[3-[4-(5-methoxy-4-pyrimidyl)-1-piperazinyl]propyl]-5-(1-oxo-4-methoxy-1,2,5-thiadiazol-3-yl)aminoindole (Example 8) (0.175 g, 0.35 mmol) in 10 mL of absolute ethanol and the resulting solution was stirred at room temperature for 1 h. The reaction mixture was then evaporated to give a yellow gum. This material was chromatographed (SiO$_2$/CH$_2$Cl$_2$-MeOH-NH$_4$OH, 90:9:1) to give a yellow gum which was subsequently treated with excess methanolic HCl. The resulting solution was evaporated and the residue was triturated with acetone to give the hydrochloride of the title compound (0.160 g, 76%) as a yellow solid, mp 158° C. (dec): IR (KBr) 3380 (br), 3200 (br), 1628, 1574, 1543 cm$^{-1}$; $^1$H NMR (DMSO-d$_6$, 200 MHz) $\delta$10.0–11.3(m, 2H), 8.64 (br s, 1H), 8.29(br s, 1H), 8.20 (br s, 1H), 7.60 (m, 1H), 7.35 (d, J=8.7 Hz, 1H), 6.96–7.22 (m, 1H), 4.89 (m, 2H), 3.90 (s, 3H), 3.62 (m, 4H), 3.16 (m, 4H), 2.77 (m, 2H), 2.14 (m, 2H). Anal. Calcd for C$_{22}$H$_{27}$N$_9$O$_2$S. 2 HCl. 2.2 H$_2$O. 0.2 CH$_4$O: C, 44.40; H, 5.74; N, 21.00. Found: C, 44.44; H, 6.14; N, 21.25.

C. Biological Test Procedures

EXAMPLE 14

Agonist Studies in the Canine Lateral Saphenous Vein

The lateral saphenous vein is obtained from an anesthetized dog and trimmed of adherent material. The vessel is then cut into 2–3 mm ring segments and mounted between stainless steel wires in tissue baths containing 20 mL of modified Kreb's buffer which is continuously aerated with 5% CO$_2$/95% O$_2$ and maintained at 37° C. Resting tension is manually adjusted to 1 gram and maintained until a stable baseline is achieved for an equilibration period of 1 h. Tissue bath solution is replaced every 15 min during this equilibration.

Ketanserin, atropine and pyrilamine are added to the baths at a concentration of 1 µM to block 5-HT$_2$, cholinergic and histaminic effects. After 15 min, with the antagonists in place, a serotonin concentration response curve is conducted in a cumulative fashion. At the conclusion, the baths are washed out several times, tension is readjusted to 1 gram and the tissue is allowed to return to equilibrium over a period of 45–60 min. The antagonists are again added to the baths and after 15 min concentration response curves are generated for selected test compounds. Individual vessel segments are only exposed to one test compound.

The activity of test compounds is expressed in terms of relative potency and efficacy compared with 5-HT (arbitrarily assigned a value of 1.0) in the same vascular preparation.

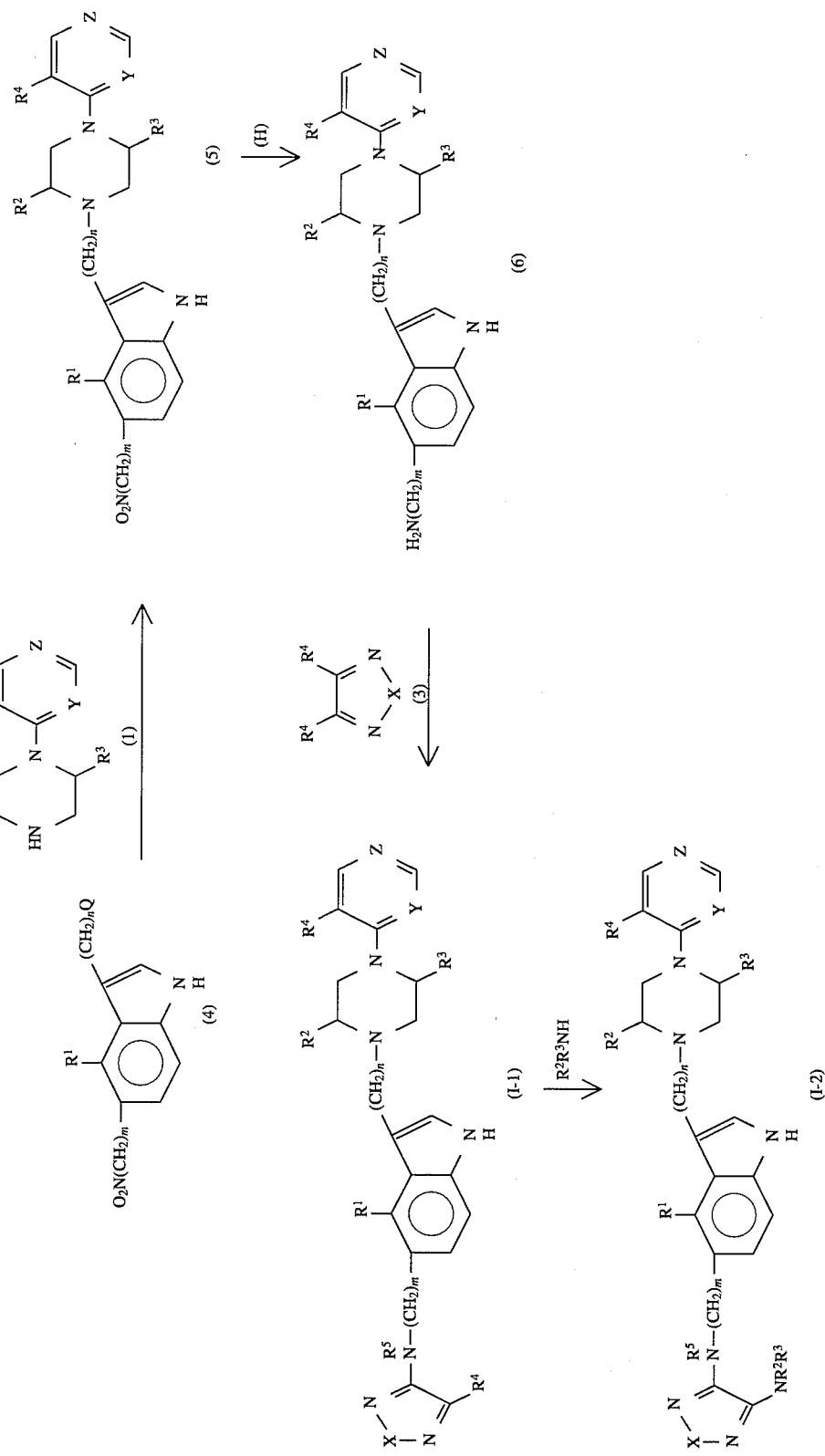

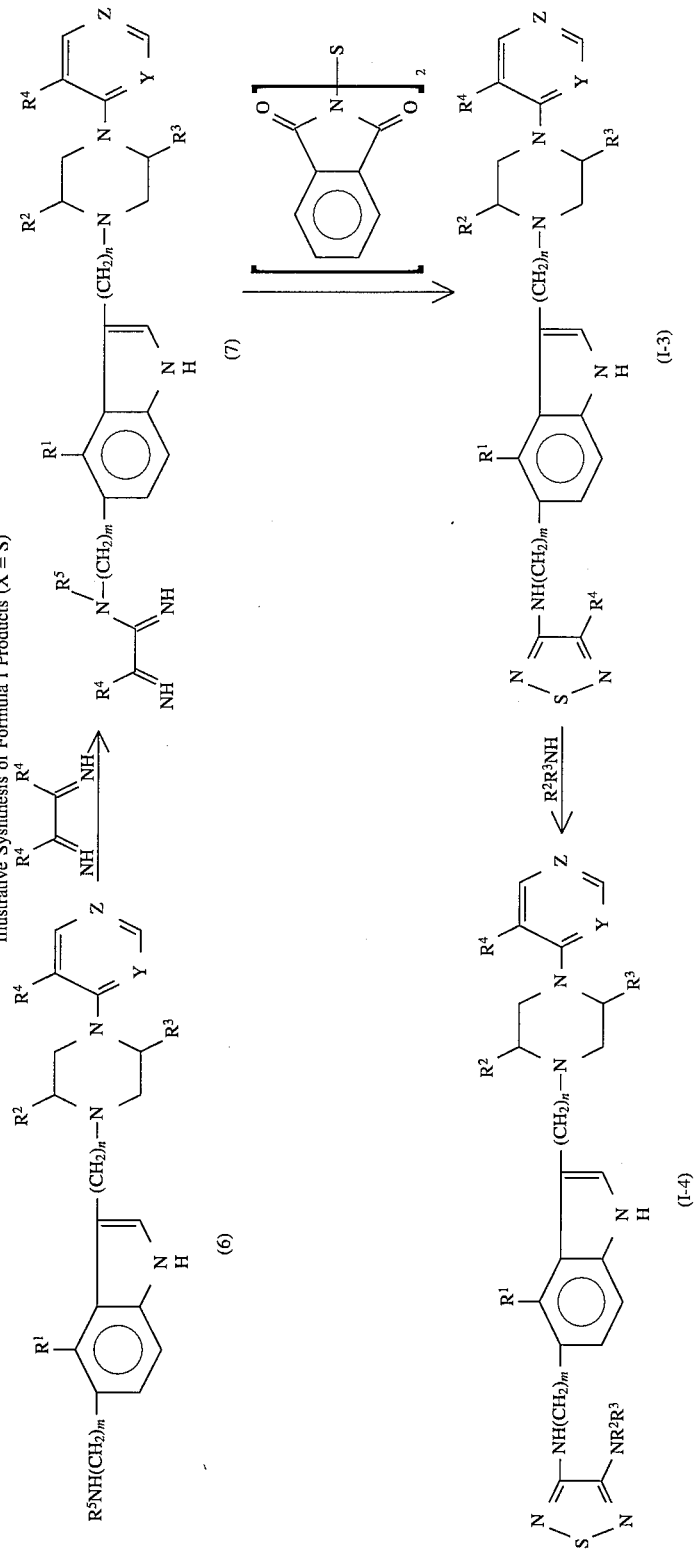

Scheme C

Syntheses of Intermediates

The following synthetic reactions are intended to provide examples of some of the available methods of preparing chemical intermediates for use in the processes of Schemes A and B.

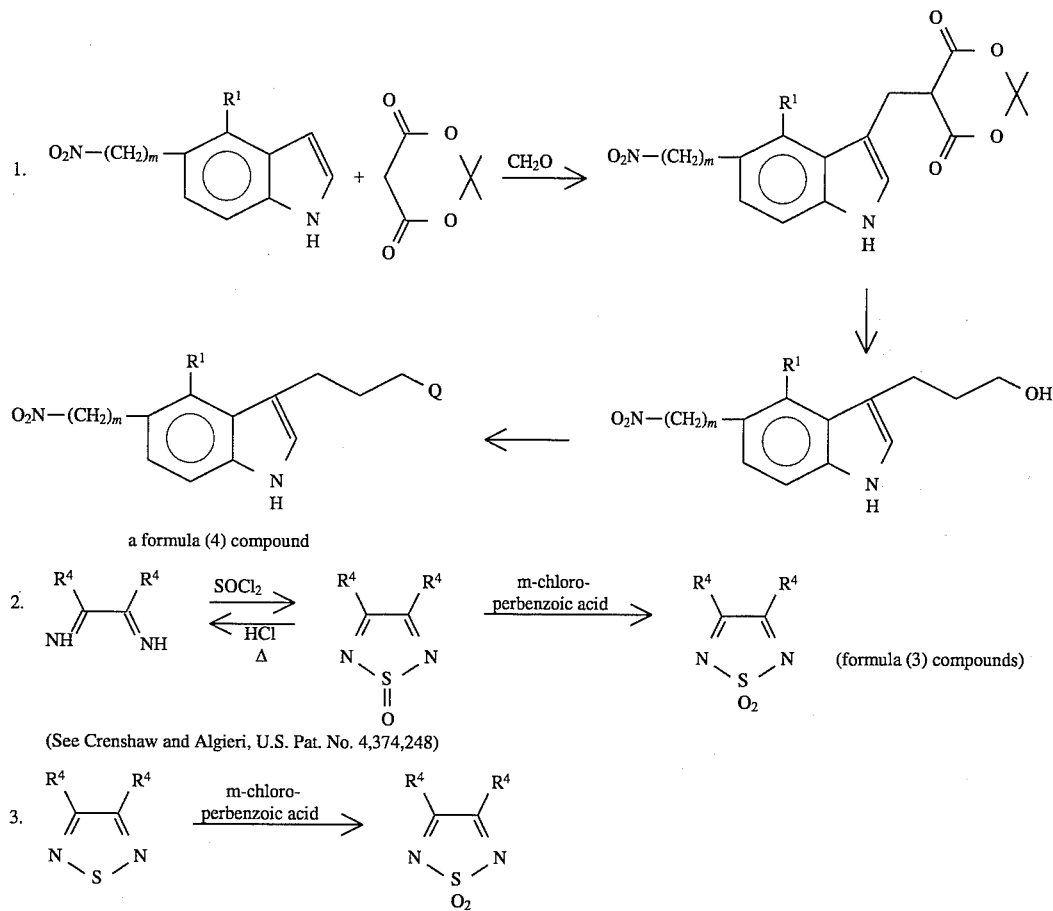

(See Crenshaw and Algieri, U.S. Pat. No. 4,374,248)

We claim:

1. A compounds of Formula I or a pharmaceutically acceptable acid addition salt and/or solvate thereof

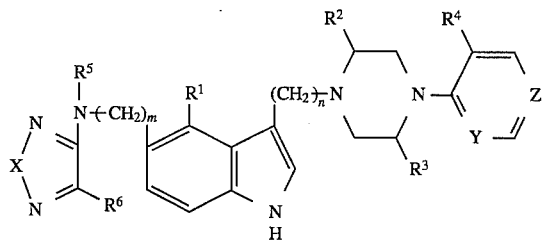

wherein $R^1$ is selected from hydrogen, halogen, lower alkyl and lower alkoxy;

$R^2$, $R^3$ and $R^5$ are independently selected from hydrogen and lower alkyl;

$R^4$ is lower alkoxy;

$R^6$ is amino, lower alkylamino, di-lower alkylamino and lower alkoxy;

X is selected from S, SO, and $SO_2$;

Y and Z are independently selected from N and CH with the proviso that both Y and Z cannot be CH simultaneously;

m is selected from zero and the integers 1 to 3; and n is selected from the integers 1 to 5.

2. A compound of claim 1 wherein Y and Z are N.

3. A compound of claim 1 wherein X is SO.

4. A compound of claim 3 wherein $R^1$, $R^2$, $R_3$ and $R^5$ are hydrogen.

5. A compound of claim 3 wherein m is zero and n is 3.

6. A compound of claim 3 wherein $R^4$ is methoxy.

7. A compound of claim 3 wherein $R^1$, $R^2$, $R^3$ and $R^5$ are hydrogen, $R^4$ is methoxy; Y and Z are N; m is zero and n is 3.

8. A compound of claim 7 selected from the group consisting of compounds wherein $R^6$ is amino, methylamino, dimethylamino, and methoxy.

9. A method for treating vascular headache by administering a therapeutically effective amount of a compound claimed in claim 1 to a person suffering from a vascular headache.

10. A method for treating vascular headache by administering a therapeutically effective amount of a compound claimed in claim 3 to a person suffering from a vascular headache.

11. A method for aborting vascular headache by administering a prophylactically effective amount of a compound claimed in claim 1 to a person suffering the onset of a vascular headache.

12. A method for aborting vascular headache by administering a prophylactically effective amount of a compound claimed in claim 3 to a person suffering the onset of a vascular headache.

13. A pharmaceutical composition in unit dosage form suitable for systemic administration to a person at risk of or suffering a vascular headache, the composition comprising a pharmaceutical carrier and from about 1 to 500 mg of a compound claimed in claim 1.

14. A pharmaceutical composition in unit dosage form suitable for systemic administration to a person at risk of or suffering a vascular headache, the composition comprising a pharmaceutical carrier and from about 1 to 500 mg of a compound claimed in claim 3.

* * * * *

UNITED STATES PATENT AND TRADEMARK OFFICE
CERTIFICATE OF CORRECTION

PATENT NO. : 5,618,816
DATED : April 8, 1997
INVENTOR(S) : Crenshaw et al

It is certified that error appears in the above-indentified patent and that said Letters Patent is hereby corrected as shown below:

On the title page, item [54] and col. 1, line 3, should read "Indolylalkyl-Pyridinyl and".

Signed and Sealed this

Twelfth Day of August, 1997

*Attest:*

BRUCE LEHMAN

*Attesting Officer*   Commissioner of Patents and Trademarks